(12) United States Patent
Albertazzi

(10) Patent No.: US 11,090,150 B2
(45) Date of Patent: Aug. 17, 2021

(54) INTRACORNEAL IMPLANT AND INJECTOR TO TREAT CORNEAL DISORDERS

(71) Applicant: Roberto Gustavo Albertazzi, Buenos Aires (AR)

(72) Inventor: Roberto Gustavo Albertazzi, Buenos Aires (AR)

(*) Notice: Subject to any disclaimer, the term of this patent is extended or adjusted under 35 U.S.C. 154(b) by 111 days.

(21) Appl. No.: 16/203,116

(22) Filed: Nov. 28, 2018

(65) Prior Publication Data

US 2019/0159888 A1 May 30, 2019

(30) Foreign Application Priority Data

Nov. 29, 2017 (AR) .................................. P170103326

(51) Int. Cl.
*A61F 2/14* (2006.01)
*A61F 2/16* (2006.01)
*A61F 9/00* (2006.01)
*A61K 9/00* (2006.01)

(52) U.S. Cl.
CPC .............. *A61F 2/147* (2013.01); *A61F 2/148* (2013.01); *A61F 2/1664* (2013.01); *A61F 9/0017* (2013.01); *A61K 9/0051* (2013.01)

(58) Field of Classification Search
CPC .......... A61F 2/147; A61F 2/148; A61F 2/167; A61F 2/1662; A61F 2/1664; A61F 2002/1682; A61F 9/0017
See application file for complete search history.

(56) References Cited

U.S. PATENT DOCUMENTS

| 2002/0072673 | A1 | 6/2002 | Yamamoto et al. |
| 2009/0137988 | A1 | 5/2009 | Kurtz |
| 2009/0306773 | A1 | 12/2009 | Silversrini et al. |
| 2016/0074155 | A1* | 3/2016 | Raquin ................. A61F 2/1672 606/107 |
| 2016/0310417 | A1 | 10/2016 | Prausnitz et al. |
| 2016/0354244 | A1* | 12/2016 | Horvath .............. A61F 9/00781 |

FOREIGN PATENT DOCUMENTS

RU 2375025 C1 12/2009

OTHER PUBLICATIONS

Office Action issued in related European Patent Application No. 18208901.1 dated Jun. 12, 2020.
"Chord (geometry)—Wikipedia" Apr. 16, 2020 URL:http://en.wikipedia.org/wiki/Chord_(geometry).

* cited by examiner

*Primary Examiner* — Ashley L Fishback
(74) *Attorney, Agent, or Firm* — Venable LLP; Michele V. Frank

(57) ABSTRACT

An injector of intracorneal segments has a disposable segment holding head comprising a lancet (36) formed with a housing closed by the lid (37) wherein a sterilized corneal segment (11) is housed, behind which there is a needle (26) longitudinally slidable under the action of a trigger (31) and a spring (32). The head also has a manual selector (38) to deflect the needle to place the segment at 90° of the head to the right or left of a channel made in the cornea for injection. The segment pre-installed in the head is provided with recesses formed by knurling (16) on its outer chord (14) where it couples to the needle for the push.

11 Claims, 7 Drawing Sheets

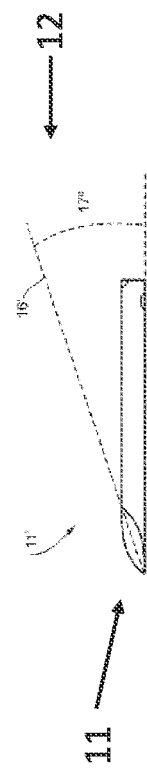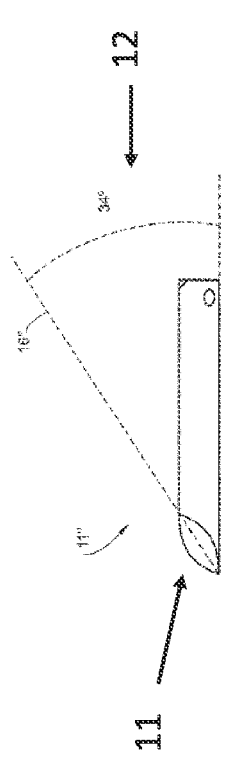

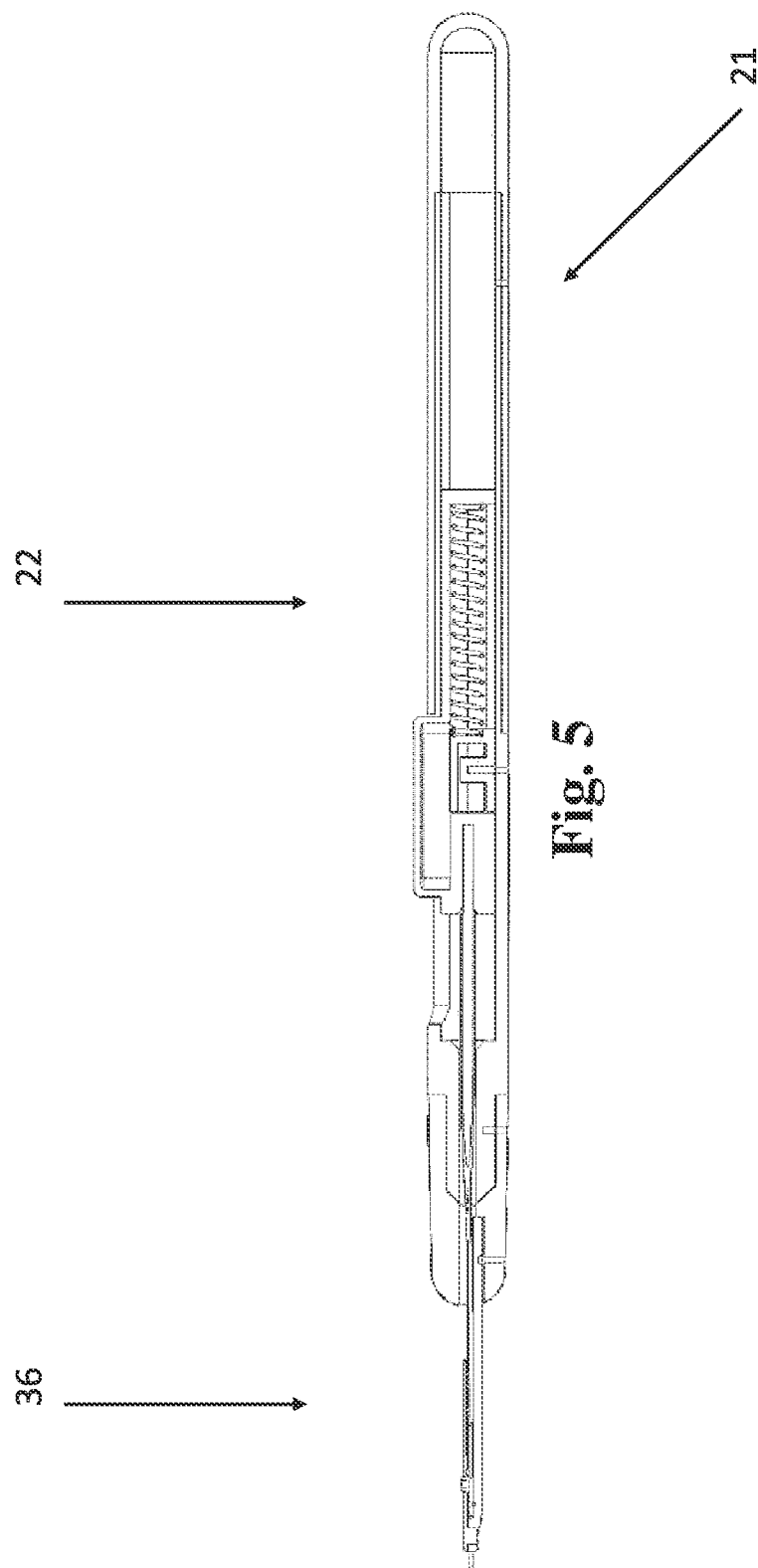

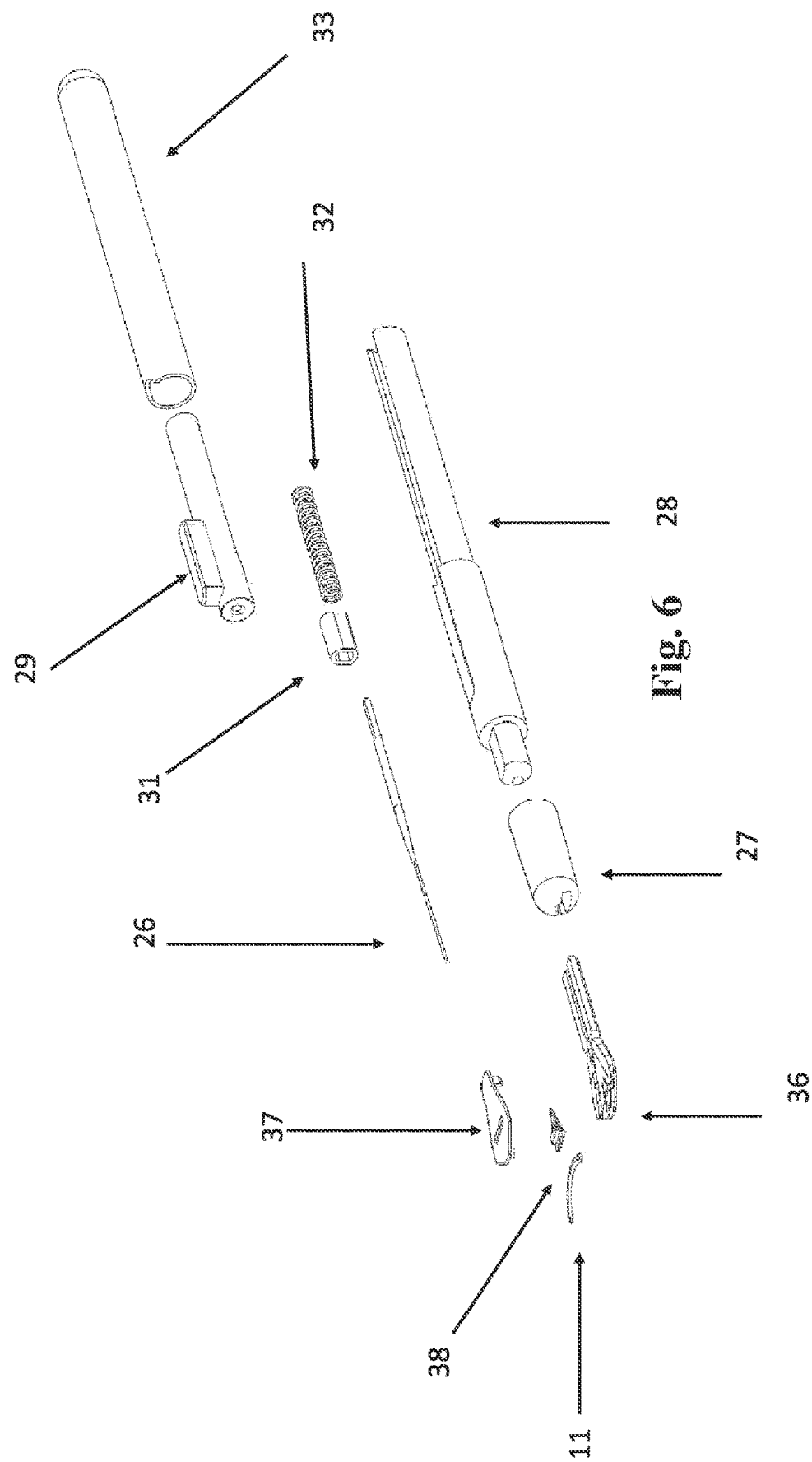

INTRACORNEAL IMPLANT AND INJECTOR TO TREAT CORNEAL DISORDERS

CROSS-REFERENCE TO RELATED APPLICATIONS

This application claims the benefit of and priority to Argentinian Patent Application No. P170103326, filed Nov. 29, 2017, the contents of which are hereby incorporated by reference in its entirety.

TECHNICAL FIELD OF THE INVENTION

The present invention belongs to the field of ophthalmological surgery and relates to an applicator instrument for rigid intrastromal inserts for the treatment of corneal ectasias (progressive deformations).

Segments or intracorneal inserts have gained a place in recent years for the treatment of ectopic diseases of the cornea for their safety and efficiency but, above all, for the ability to improve vision without correction of these patients. These segments are not usually easy to manipulate manually for their dimensions to be inserted and the instrument that is proposed helps in this field.

STATE OF THE ART AND PROBLEMS TO BE SOLVED

The treatment consists in placing intracorneal inserts in the form of arc segments within the stroma (the corneal body itself). To install them a channel is created parallel to the corneal surface of about 80% of the corneal thickness or 150 µm (micrometers) of the corneal endothelium is left. The creation of this channel is usually done with the assistance of a FemtoLaser used for this purpose in ophthalmologic surgery or it can be done with the help of a semicircular spatulas after an incision with a precalibrated scalpel to the desired depth. US Publication No. 2009/137,988 (LenSx) describes techniques and systems for performing optical function by means of a laser.

Manipulating the intracorneal segments is not easy due to the tiny size of the implant, the visibility of the implant and the rigidity of its material, apart from the different types of containers that do not always place the insert in its place.

The Russian patent (RU) No. 2,375,025 (Federal Noe G Uchrezhdenie MNT) refers to the effect of rings on the cornea and the effect of keratoconus.

US publication (US) No. 2002/72,673 (Yamamoto) refers to an apparatus for guiding substances or devices towards the Schlemm's canal to relieve ocular pressure in the treatment of glaucoma so that the surgery is minimally invasive.

US publication (US) No. 2016/310417 (Emory University) refers to formulations, systems and methods of administration for injecting drugs or placing ocular tissue in the suprachoroidal space through microneedles.

In relation to intracorneal segments, US publication (US) No. 2009/306,773 (AcuFocus) teaches implants that block the transmission of light with the aim of altering the refractive properties of the cornea.

Currently there are ophthalmic surgeons who practice the operation with the help of forceps modified for this purpose. These forceps have a curvature designed to achieve a better "grip" of the segments. Once the initial part of the segment is inserted into the tunnel, a handle with a thin tip called Sinskey is used. This tip is inserted into the segment's appendage and a torsional force is generated to finish inserting the segment. FIG. 1A illustrates a McPherson-Albertazzi type forceps and FIG. 1B a Sinskey type tip.

That is to say, it is not known in the literature or in practice, except for the aforementioned forceps, devices that allow to inject, that is to say to place and insert directly, rigid intracorneal segments to treat ectatic diseases of the cornea.

SUMMARY OF THE INVENTION

One of the most difficult and main objective problems posed by the invention is how to inject a rigid material, as opposed to injecting a liquid or a gel, with an instrument with the dimensions that enter a needle. Another object of the invention is to manufacture an instrument capable of injecting different types of intracorneal segments whatever their parameters such as arc, profile, thickness and diameter are.

The injector of the present invention is a rigid material delivery instrument that is used to manually slide the intracorneal segment. It includes a segment container holding inside the preloaded segment, sterile and ready for use. The container is placed in front of a handle to push the insert and contains a kind of sword or modified Sinskey hook, which is used to slide the segment. The handle has the following parts: needle, pointer, body, stop, trigger, spring and cover. The slider head that holds the segment has the following different parts: lancet, lid, selector and the segment or corneal insert itself that it is preloaded in the instrument and injected from the same, without having to touch it with any forceps or other instrument, solving an important problem if, on the contrary, segments with these characteristics had to be manipulated (dimensions, static electricity, etc.).

The segment can be placed or delivered at 90° of the head either to the right or the left manually according to the position of a selector mounted on the handle. The base of the injector is designed with three different inclinations of 0°, 17° and 34° depending on the profile of the segment used and preloaded. Thanks to its design, the instrument allows to inject the segments or implants either to the right or to the left of the channel where it will be housed, without touching the segment or the danger that it jumps, because it is fixed and housed inside the instrument preventing any sudden movement as may occur with a forceps.

Furthermore, the present invention also teaches to add knurls forming recesses in the outer chord to improve or facilitate the thrust of the instrument without losing the physiological functionality.

Having the tunnel with the exact dimensions and the precise place and a pre-established diameter that surrounds the visual axis in 5; 6 or 7 millimeters, the segments are injected with the help of the instrument. The segment is introduced through the incision and, once the segment is with its end in the desired place, it is injected with the help of the trigger which, when moved forward, moves the needle, which, through the right-left selector previously selected, is housed in the knurls of the segments to inject the implant into the tissue, either towards the temporal part of the cornea as the nasal portion, up or down, right or left, indistinctly.

Once the segment is implanted in a cornea, the sliding part where the implant was housed can be separated from the end of the handle and discarded. The handle that houses the modified Sinskey hook can be resterilized to be reused on other occasions.

DESCRIPTION OF THE DRAWINGS

In order that the present invention is clearly understood and easily implemented, it is presented according to one of its preferred embodiments in the attached illustrative and non-limiting figures, wherein:

FIG. 3A is a side elevational view of the intracorneal segment of FIG. 2. FIGS. 3B and 3C are analogous views in side elevation of similar segments but with inclinations of 17° and 34°, respectively.

FIGS. 5 and 6 are longitudinal and exploded cross-section views, respectively, of the injector of FIG. 4.

DETAILED DESCRIPTION OF THE INVENTION

Figure 1A:
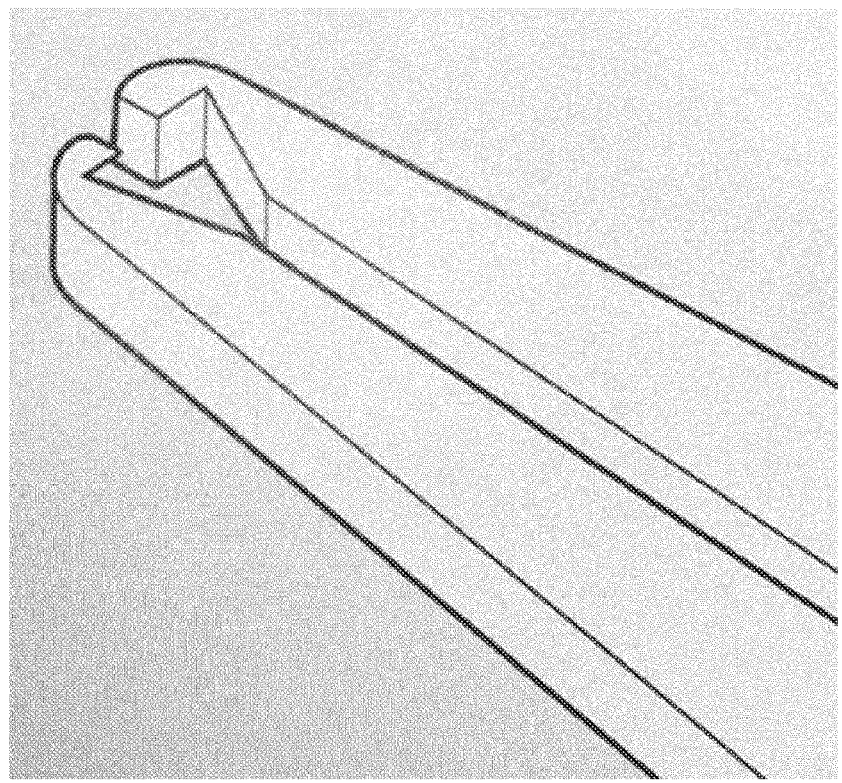
FIGS. 1A and 1B are perspective views of a known McPherson-Albertazzi forceps and a Sinskey tip, described above.
Figure 1B:
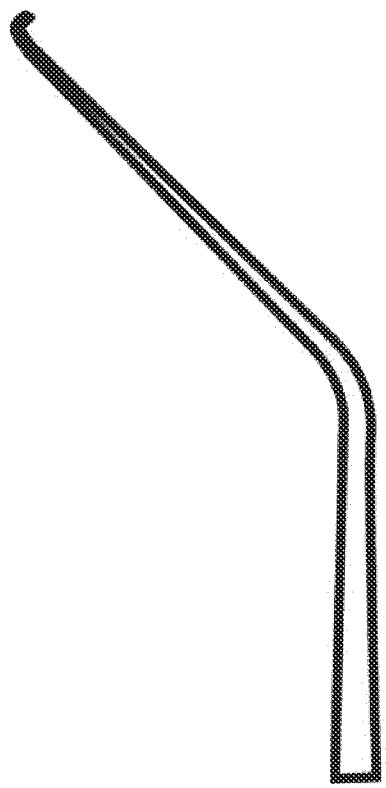
Figure 2:
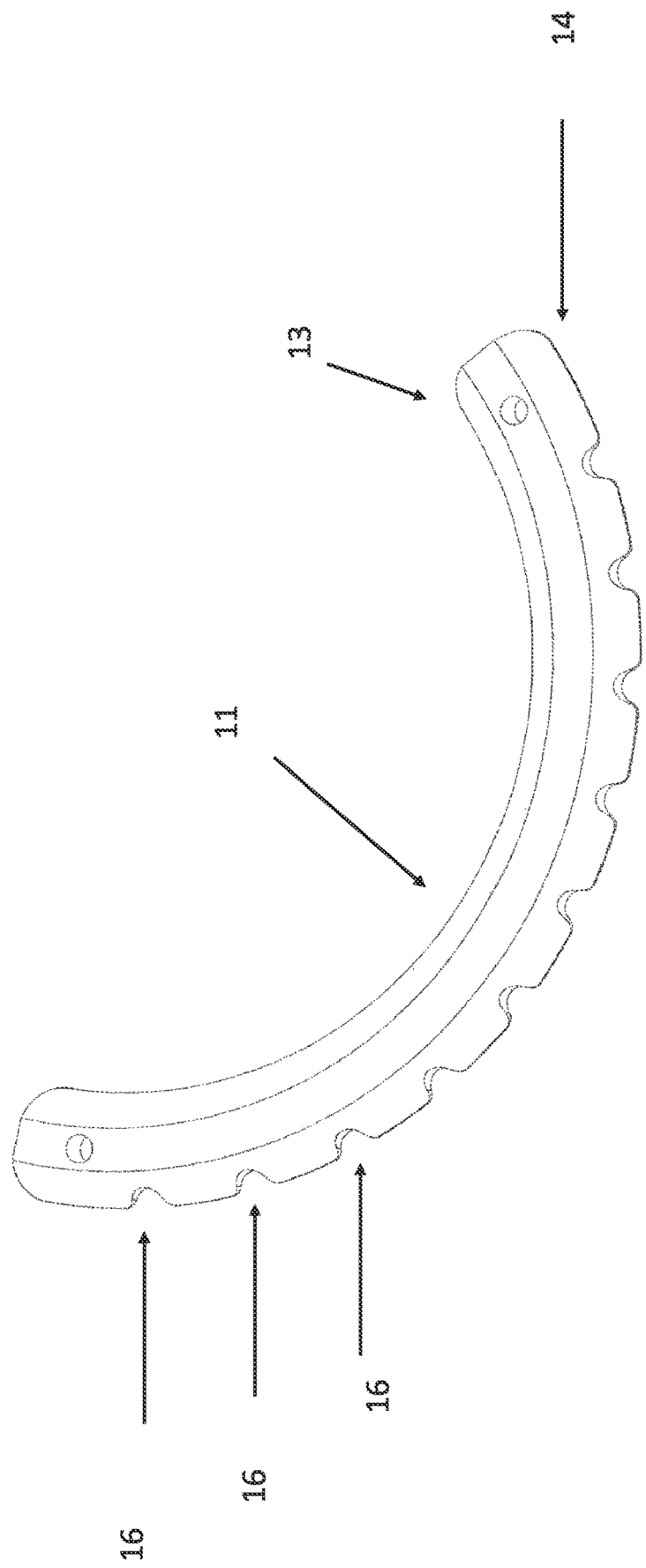
FIG. 2 is a perspective view of an intracorneal segment according to the invention without inclination.

FIGS. 2 and 3A show an intracorneal insert or implant 11 of a rigid material such as medical grade CQ transparent acrylic or PMMA (PolymethylMethacrylate); alternatively, it can be manufactured with Prolene or another plastic material compatible with corneal metabolism. The intracorneal insert 11 has the shape of a circular segment of 135° measuring 0.15 mm in plan, having a constant thickness in the medial plane arc 12, gradually flaring to the inner 13 and outer 14 chords of the segment 11.

This insert 11 has an inclination of 0°, i.e. it has no inclination. In FIG. 3B a similar insert 11' is shown but the inclination 16' is 17° and FIG. 3C shows another similar insert 11" with an inclination 16" of 34°. The inserts 11 can have 5; 6 or 7 mm central diameter. The dimensions of the segments are critical with a tolerance of +/−15 μm (micrometers) to have predictable results. The description so far is applicable to conventional inserts such as those manufactured by Ferrara Ring, Intacs and Keraring wherein the surface of the outer chord is smooth.

According to an aspect of this invention, the conventional segment is modified by a knurling of the outer chord 14 to form small recesses 16 to improve the pushing and implantation capability of the injector 21 described in the following paragraphs. The recesses 16 are about ten and are equidistantly distributed.

Figure 4:
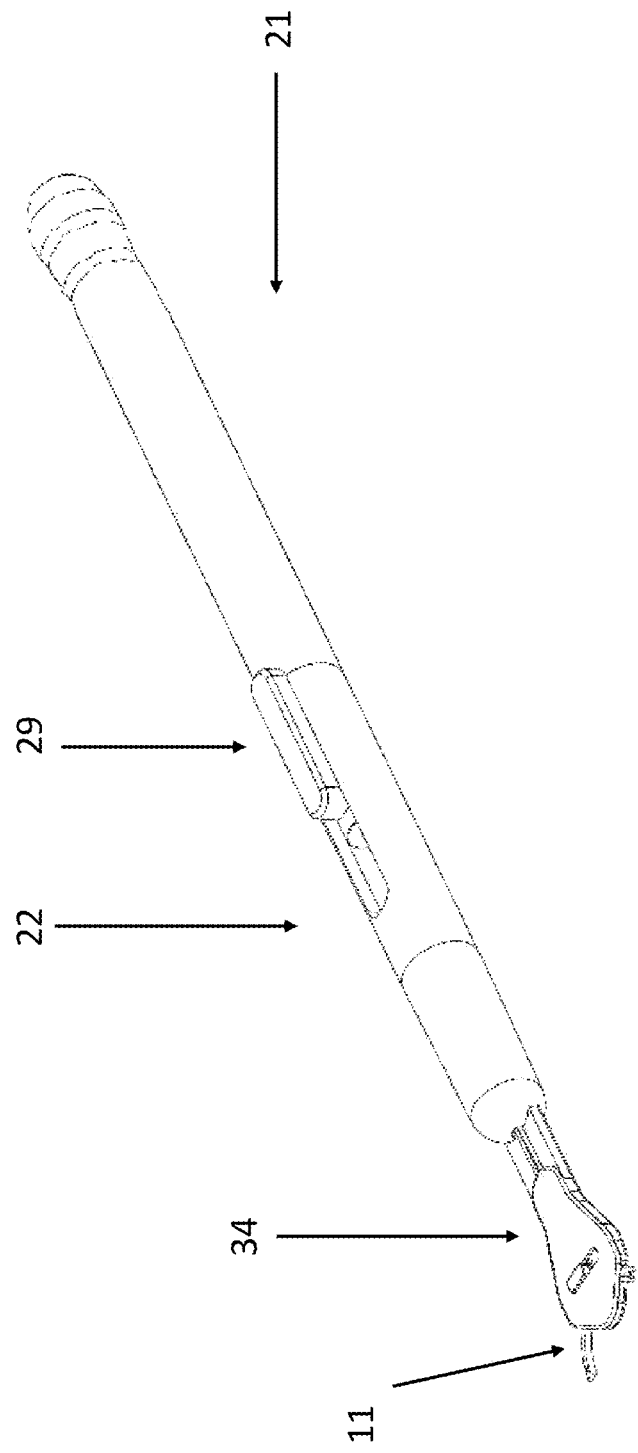
FIG. 4 is a perspective view of a preferred embodiment of an intracorneal segment injector according to the invention.

FIGS. 4 to 6 show the injector 21 that can be used for implanting the segment 11 of FIG. 2 in a cornea according to the main object of the present invention. It is a rigid material delivery instrument that is used to manually slide the intracorneal segment 11.

The injector 21 consists of two parts: a handle 22 used to push the segment 11 and a head 34 placed in front of a handle 22 and containing the segment 11. The head 34 is disposable: it is discarded once the end where the segment 11 was housed is used. The handle 22 is re-sterilizable for reuse in future occasions.

The handle 22 is formed by a needle 26, a pointer 27, a body 28, a stop 29, a trigger 31, a spring 32 and a cover 33. The pointer 27 is the coupling piece with the head 34, which is basically a container 22 that houses the preloaded intracorneal segment 11, sterile and ready for use. The head 34 comprises a segment holding lancet 36, a lid 37, a selector 38 and the corneal segment 11 itself housed within a cavity defined between the segment holding lancet 36 and the lid 37.

The interior of the lancet 36 is shaped to retain the corneal segment 11 together with the lid 37. The base of the lancet 36 is designed with three different inclinations of 0° (coplanar), 17° or 34° (actual inclination) according to the profile of the segment used and preloaded.

The pointer 27 is coupled to the body 28 of the handle, and inside a needle 26 longitudinally runs forward under the pressure of the spring 32 when the trigger 31 is pulled. Behind the corneal segment 11 is the portion of the selector 38 which protrudes by a transverse slot in the lid so that it can be moved from left to right and vice versa. The segment 11 can be placed or delivered at 90° of the head either to the right or the left, depending on the position of the selector 38, that is manually selected. The position of the selector 38 determines if the needle 26 deflects to the left or right when it is pushed forward.

The body 28 has a rear protrusion wherein the spring 32 is housed and which penetrates inside the cover 33 to which it is attached.

To inject, the surgeon moves the trigger 31 forward, moving the needle 26 by placing it in the knurls 16 of the segments 11 to inject the implant into the tissue, either towards the temporal part of the cornea or the nasal portion, upwards or downwards, to the right or left according to the position of the right-left selector 38 previously selected.

What is claimed is:

1. An injector for implanting intracorneal segments in a treatment of corneal disorders, the injector comprising a handle shaped to push an intracorneal segment and a slider head mounted in a front end of the handle, the slider head having a segment holder for receiving the intracorneal segment, wherein the segment holder is a lancet defining a cavity closed by a lid, with the intracorneal segment being housed in said cavity under the lid, said injector further comprises a needle, longitudinally slidably mounted in the handle, and a trigger and a spring placed behind the needle which can actuate said needle, and wherein the slider head further includes a manual selector to place the intracorneal segment at 90° of the slider head to the right or left of a channel made in a cornea to be injected.

2. The injector according to claim 1, characterized in that the slider head is preloaded with a sterile and ready for use intracorneal segment.

3. The injector according to claim 1, wherein the slider head with the segment holder form an assembly detachable from the handle.

4. The injector according to claim 1, wherein the manual selector is a part located in the path of the needle to deflect it towards one or the other side of the slider head, the manual selector including a manual portion protruding through a transverse slot in the lid.

5. The injector according to claim 1, wherein the handle houses, in addition to the needle, the spring and the trigger coupled to the needle to drive it longitudinally.

6. The injector according to claim 1, wherein the lancet has a base formed with an inclination between 0° and 34° according to the profile of the intracorneal segment.

7. The injector according to claim 1, wherein the slider head with the segment holder are disposable.

8. An intracorneal segment delivery system comprising the injector according to claim 1, and an intracorneal segment having a shape with respective inner and outer chords, and the intracorneal segment is made of only one circular or at least partially circular piece having an outer chord provided with recesses for pushing the intracorneal segment into a cornea.

9. The intracorneal segment delivery system according to claim 8, wherein the recesses in the outer chord are formed by knurling.

10. The intracorneal segment delivery system according to claim 8, wherein the intracorneal segment is rigid.

11. The intracorneal segment delivery system according to claim 8, wherein the intracorneal segment presents a constant thickness in a medial plane arc, gradually flaring to the inner and outer chords of the intracorneal segment.

\* \* \* \* \*